US00PP10893P

United States Patent [19]

Strode

[11] Patent Number: Plant 10,893

[45] Date of Patent: May 11, 1999

[54] SPATHIPHYLLUM PLANT NAMED '31581'

[75] Inventor: Randall E. Strode, Apopka, Fla.

[73] Assignee: Agri-Starts, Inc., Apopka, Fla.

[21] Appl. No.: 08/863,465

[22] Filed: May 27, 1997

[51] Int. Cl.[6] ..... A01H 5/00

[52] U.S. Cl. ..... Plt./364

[58] Field of Search ..... Plt./88.1, 364

[56] References Cited

U.S. PATENT DOCUMENTS

P.P. 10,146 12/1997 Caldwell ..... Plt./88.1

P.P. 10,246 2/1998 Cornelis ..... Plt./88.1

*Primary Examiner*—Howard J. Locker

*Attorney, Agent, or Firm*—Driggs, Lucas, Brubaker & Hogg Co., L.P.A.

[57] ABSTRACT

A new and distinct cultivar of *Spathiphyllum* plant having darker and more rounded leaves and a greater compactness than other varieties and by having a greater suckering propensity than its parents and more resistance to the burn problems than the pollen parent.

1 Drawing Sheet

BACKGROUND OF THE DISCLOSURE

This invention relates to a new and distinct plant variety of the Araceae family and, specifically, to a new and distinct plant variety of *Spathiphyllum* which is named *Araceae Spathiphyllum* '31581'.

Certain plant varieties of the Araceae family are well known in the foliage plant market and among these is the 'Viscount' variety of the *Spathiphyllum*. This variety is characterized by, among other things, foliage with leaf blades that have a solid green field and an inflorescence with a spathe of white tending to a pure snow white.

The variety forming the subject matter of this application is hybrid of interspecific genetic background from a cross between 'Viscount' (unpatented) and 'Petite' (unpatented). A general objective of the invention has been to provide a variety of the *Spathiphyllum* genus which would be distinguishable from the other known varieties of this species and suitable for sale in the foliage plant marketplace.

This new variety of *Spathiphyllum* was asexually reproduced by tissue culture near Apopka, Fla. and such reproduction has shown this new variety to come true in successive generations. This propagation of the new variety by tissue culture in the usual controlled environment clearly shows the continued maintenance of the characteristics described herein which distinguish this new variety from the parent varieties and all other known and related varieties mainly by the darker and more rounded, less elongated and thicker leaves and its greater resistance to the burn problems associated with 'Petite'. The length of the leaves is about 20% greater than their width. Furthermore, this novel variety has about a 30% greater propensity to sucker than do its parents. The length of the peduncles is about 30% less than that of the parents, thus contributing to a compact size, thereby adding to its overall attractiveness and facilitating the packaging of the same for shipment.

BOTANICAL DESCRIPTION OF THE PLANT

All color references below are measured against The Royal Horticultural Society Colour Chart. Colors are approximate as color depends on horticultural practices such as light level and fertilization rate, among others.

BRIEF DESCRIPTION OF THE PHOTOGRAPH

The accompanying color photographic illustration shows, as nearly true as it is reasonably possible in a color illustration of this character, the whole plant grown in a pot.

Parentage:

*Seed parent.*—*Spathiphyllum* 'Viscount'.

*Pollen parent.*—*Spathiphyllum* 'Petite'.

Plant:

*Form.*—Bush.

*Growth.*—Vigorous.

*Height.*—Approximate measurements of average: 18" to 24" (46–61cm) in a six inch pot, measured from the soil surface to the top of the most recently unrolled spathe and 15" from the soil surface to the top of the most recently unfolded leaf. Measurement is taken at first flowering when the plant is 7–9 months old.

*Spread.*—24" (61cm) in a six inch pot.

*Time from liner to market size.*—7 to 9 months.

Foliage:

*Color.*—147A Green.

*Size.*—Leaves are medium measuring 4" to 4¾" (10–12 cm) wide and 6.7" (17cm) long. Length about 20% greater than width.

*Quantity.*—Abundant.

*New foliage color.*—Upper side 141A Green; Under side 137C Green.

*Shape.*—Lanceolate.

*Texture.*—Upper side is smooth.

*Thickness.*—Thicker than those of parents.

*Gloss.*—About 50% more than other members of the species. Ribs and veins are prominent; Edge is smooth. Midrib is flat and same coloration as leaf.

*Leaf stem.*—Color 137A Green; Under side is smooth; Stipules-None.

*Resistant to disease.*—Typical for the species. Width — ¼" to ½" at base. Color — Dark green (137A).

*Geniculum.*—Bent at 15° angle and thickened. Color is 137A.

*Resistance to burn.*—Substantially better than that of the pollen parent.

*Attitude.*—Horizontal or slightly ascending at maturity.

Inflorescence

Blooming habit:

*Blooms.*—Profusely, recurrent — Spring and Fall. Will bloom in 9–11 weeks when treated with gibberellic acid. Bloom lasts about 20 days.

Bud:

*Color.*—157B White.

*Size.*—2" to 2.4" (5–6 cm) long and small.

Peduncle: Medium length of 12–15 inches, width of 3/16–1/4 inches, nested in foliage, smooth, erect and slender.

*Length.*—About 30% less than comparable length of parents and other members of the species.

*Color.*—White 157B. Bud opens well and not affected by adverse conditions.

Spathe:

*Color.*—155D white; turns green 145B after 21–30 days.

*Texture.*—Thick, leathery, and not affected by wet or hot weather.

*Appearance.*—Inside and outside are satiny.

*Form.*—Oval and pointed.

*Attitude.*—Upright, parallel to spadix.

*Symmetry.*—Uniform.

*Margin characteristics.*—Smooth.

*Length.*—4".

*Width.*—2.3".

*Arrangement.*—Single spadix.

*Persistence.*—Hang on for 3–4 weeks depending on temperature and daylight.

*Apex.*—Slightly curled, similar to other members of the species.

Spadix:

*Spadix.*—Small.

*Color.*—Male 155A White; Female 158B White.

*Length.*—2".

*Width.*—1/2".

Reproductive organs:

*Perianth.*—Shape, size, and white color not unlike those of the genus per se.

*Corolla.*—White and minute, typical of the genus.

*Androecium.*—Filaments white; not normally easily visible until pollen release. Size and character are within the normal range for the genus. Anthers and pollen are white.

*Gynoecium.*—Color is white; stigma is exposed after exposure of spadix; minute and not readily discernible without magnification.

*Pollen.*—Color 155D White.

*Styles.*—Columnar, even, heavy, and short in length.

*Ovaries.*—White, and are enclosed in calyx. They are not readily visible without magnification and dissection of the flower.

Fruit: Fertile.

*Form.*—Seeds protruding.

I claim:

1. A new and distinct cultivar of *Spathiphyllum* plant as herein shown and described, characterized particularly as to novelty by having darker and more rounded leaves and greater compactness than other varieties and by having a greater suckering propensity than its parents and more resistance to the burn problems than the pollen parent.

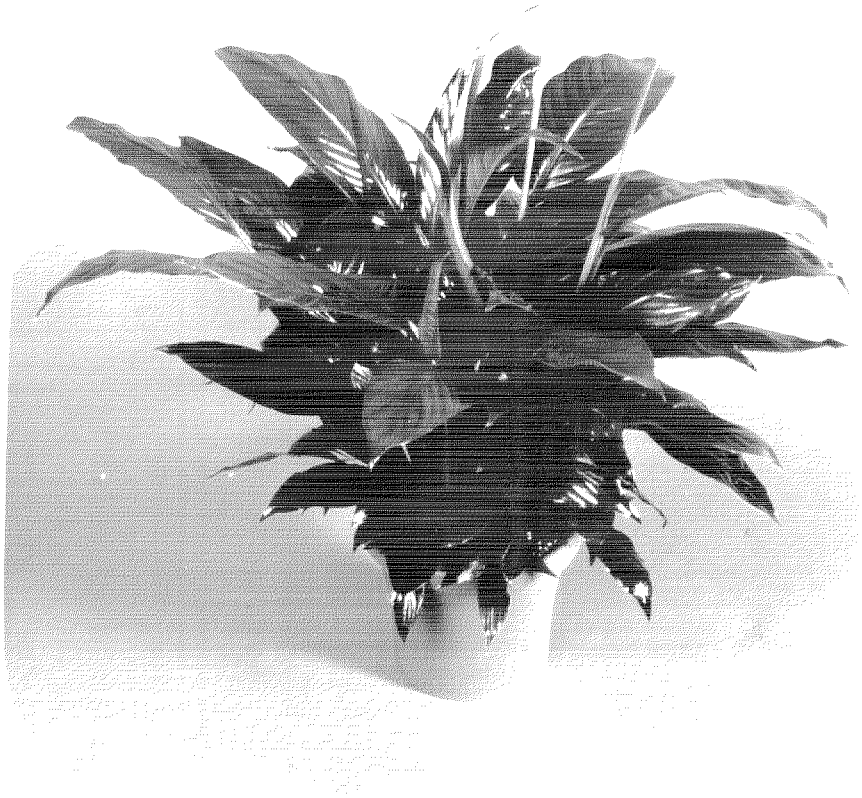

* * * * *